(12) United States Patent  
Myers

(10) Patent No.: US 7,479,144 B2
(45) Date of Patent: Jan. 20, 2009

(54) COLLAPSIBLE ORTHOPAEDIC REAMER

(75) Inventor: Reese Myers, Warsaw, IN (US)

(73) Assignee: Symmetry Medical, Inc., Warsaw, IN (US)

(*) Notice: Subject to any disclaimer, the term of this patent is extended or adjusted under 35 U.S.C. 154(b) by 606 days.

(21) Appl. No.: 11/009,119

(22) Filed: Dec. 10, 2004

(65) Prior Publication Data

US 2006/0149270 A1 Jul. 6, 2006

(51) Int. Cl.
A61B 17/16 (2006.01)

(52) U.S. Cl. ........................................ 606/80
(58) Field of Classification Search ........... 606/79, 606/80, 81, 84, 85
See application file for complete search history.

(56) References Cited

U.S. PATENT DOCUMENTS

| 2,649,001 | A | 8/1953 | Fennell |
| 3,702,611 | A | 11/1972 | Fishbein |
| 4,131,116 | A | 12/1978 | Hedrick |
| 4,162,867 | A | 7/1979 | Calcaterra et al. |
| 4,271,849 | A | 6/1981 | Rehder |
| 4,946,461 | A | 8/1990 | Fischer |
| 5,445,639 | A | 8/1995 | Kuslich et al. |
| 6,106,536 | A | 8/2000 | Lechot |
| 6,409,732 | B1 | 6/2002 | Salyer |
| 6,723,102 | B2 | 4/2004 | Johnson et al. |
| 2002/0133153 | A1 | 9/2002 | Hyde, Jr. |
| 2003/0212402 | A1 | 11/2003 | White et al. |
| 2003/0220647 | A1 | 11/2003 | McCallum et al. |
| 2003/0229356 | A1 | 12/2003 | Dye |
| 2003/0236523 | A1 | 12/2003 | Johnson et al. |
| 2004/0097947 | A1 | 5/2004 | Wolford et al. |
| 2004/0143271 | A1 | 7/2004 | Wolford |
| 2004/0167528 | A1 | 8/2004 | Schantz |
| 2004/0172036 | A1 | 9/2004 | Dye |
| 2004/0225294 | A1 | 11/2004 | Fredrick et al. |
| 2005/0038443 | A1 | 2/2005 | Hedley et al. |
| 2005/0075639 | A1 | 4/2005 | Lechot |
| 2005/0113836 | A1 | 5/2005 | Lozier et al. |

Primary Examiner—Eduardo C Robert
Assistant Examiner—David Comstock
(74) Attorney, Agent, or Firm—Taylor & Aust, P.C.

(57) ABSTRACT

An orthopaedic reamer including an at least partially hemispherical cutting head which is rotatable about a primary axis and at least one deployable wing connected to the cutting head. Each of the deployable wings are pivotable about a corresponding secondary axis. At least one corresponding secondary axis is in the same plane as the primary axis.

17 Claims, 3 Drawing Sheets

US 7,479,144 B2

COLLAPSIBLE ORTHOPAEDIC REAMER

BACKGROUND OF THE INVENTION

1. Field of the Invention

The present invention relates to orthopaedic reamers, and, more particularly, to reduced profile orthopaedic reamers.

2. Description of the Related Art

Minimally invasive surgery includes procedures that accomplish the elements of surgery (diagnosis, staging, resection, and repair, for example) with a minimal amount of psychological and somatic trauma. The technological procedures available for use by surgeons include methods for operating on patients with ever-smaller incisions, less operative risk, and quicker recoveries.

In total-hip replacement surgery, for example, the hip socket or acetabulum and the femoral head are typically badly deteriorated due to arthritis, or some other condition. In elderly patients particularly, this diseased condition dictates the removal of the head (ball) of the femur and its replacement by a polished metal (or other suitable material) ball with a shaft anchored in the intramedullary canal of the femur. To provide a proper bearing surface for the ball, one that will not limit the normal motion of the leg, it is necessary to reform the normal socket, or acetabulum, reaming away the diseased bone and cartilage to make a new structural base to receive a metallic or plastic (or other suitable material) socket matched to the artificial femoral head. The artificial socket is affixed within the reformed acetabulum by way of a suitable cement.

In shaping the acetabulum to receive the artificial socket, the acetabulum is undercut with an orthopaedic reamer so as to provide a surface against which the cement and artificial socket are seated and thus anchored to the bony structure of the acetabulum. Acetabular reamers are surgical tools, which are used to cut hemispherical cavities in the acetabulum for the insertion of artificial hip joint socket as described above. An acetabular reamer is typically composed of an acetabular reamer cup mounted on a tool driver, which in turn is mounted in the chuck or collet of a portable drill or flexible powered shaft. Acetabular reamer cups have an arrangement of precisely shaped cutting surfaces extending outwardly from an essentially hemispherical shell. Acetabular reamer cups are separable from their tool drivers for changing cup size prior to or during surgery, cleaning, and/or sharpening.

Acetabular reamers must be capable of producing cavities with very close tolerances. Acetabular reamer cups have precise dimensions and are light in weight and must fit on an appropriate tool driver with a minimum of free play and must be quick and easy to install and remove preferably without tools.

Because of the differing sizes, ages and physiologies among hip replacement patients, reamers of differing sizes are required. Hemispherical reamers are known which have diameters in the approximate range of 1.0 inches to 2.5 inches and which require a corresponding incision. If the reamer profile, which is introduced to the incision, can be reduced then the incision can be reduced thereby facilitating a more minimally invasive surgery.

Reamers are known which have portions of the hemisphere removed to reduce the profile presented to the incision and which thereby fit into the incision with less damage to soft tissue. However, these reamers have undesirable cutting performance such as eccentric cutting, uneven action and edges that catch on protruding anatomy. This undesirable cutting performance is due to the resulting reamer geometry after the portions are removed, which creates a rotationally unbalanced and unstabilized reamer geometry.

What is needed in the art is an orthopaedic reamer, for minimally invasive surgery, with a reduced profile and which has minimal or no degradation in cutting performance.

SUMMARY OF THE INVENTION

The present invention provides a reduced profile orthopaedic reamer with deployable wings.

The invention comprises, in one form thereof, an orthopaedic reamer including an at least partially hemispherical cutting head which is rotatable about a primary axis and at least one deployable wing connected to the cutting head. Each of the deployable wings are pivotable about a corresponding secondary axis. At least one corresponding secondary axis is in the same plane as the primary axis.

An advantage of the present invention is that it provides a reduced profile for minimally invasive surgery.

Another advantage of the present invention is that it has minimal or no degradation in cutting performance.

Yet another advantage of the present invention is that it requires no additional force to actuate the deployable wings.

Yet another advantage of the present invention is that it requires no additional tools to actuate the deployable wings.

Yet another advantage of the present invention is that it requires no additional action to actuate the deployable wings.

Yet another advantage of the present invention is that it provides a rotationally balanced and stabilized reamer when the deployable wings are pivoted to an operating position.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION OF THE INVENTION

Figure 1:
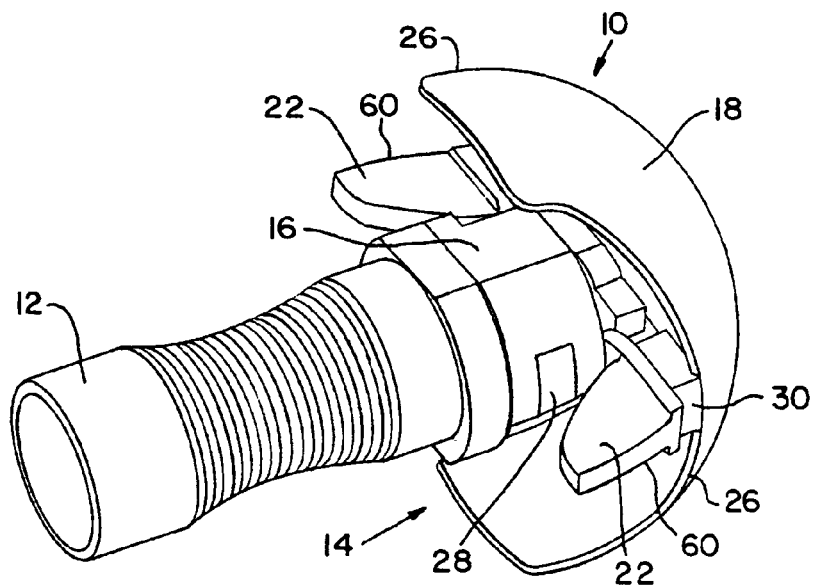
FIG. 1 is a perspective view of an embodiment of an orthopaedic reamer assembly of the present invention, shown with wings pivoted in an operating position.
Figure 2:
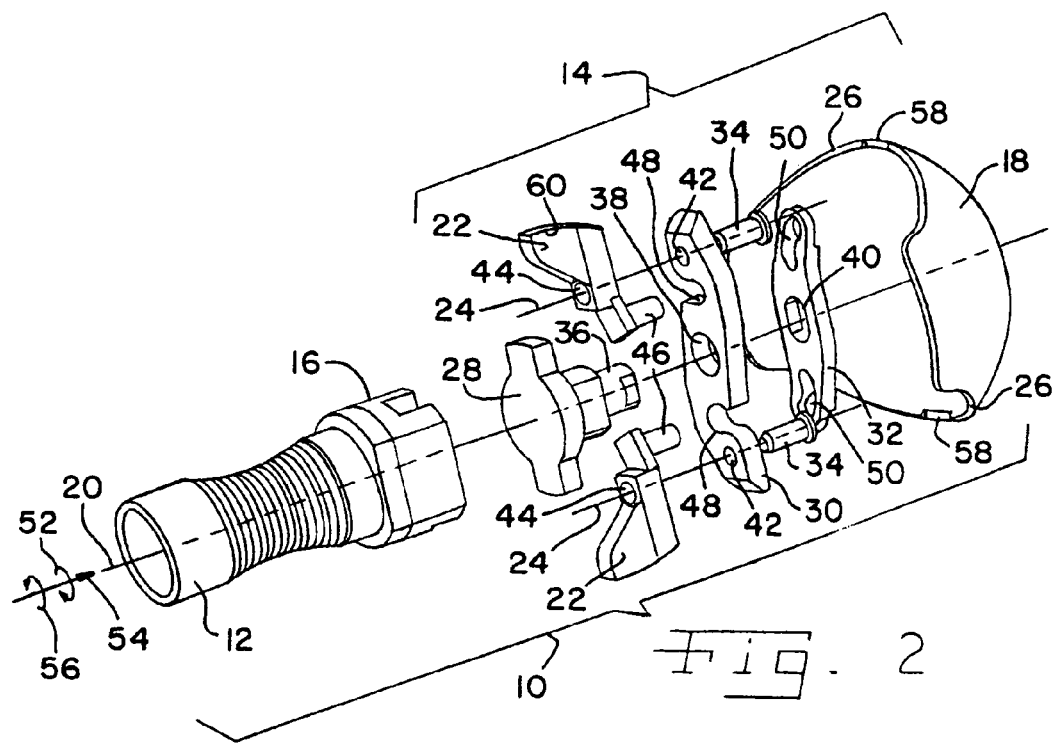
FIG. 2 is an exploded perspective view of the orthopaedic reamer assembly of FIG. 1.

Referring now to the drawings, and more particularly to FIGS. 1 and 2, there is shown a orthopaedic reamer assembly 10 which generally includes a driver 12 and an orthopaedic reamer 14 connected to driver 10.

Driver 10 is typically connected at one end to a chuck or collet of a portable drill or flexible powered shaft or other rotating tool (not shown). Driver 10 includes at the other end reamer attachment 16 which connects to reamer 14.

Reamer 14 includes an at least partially hemispherical cutting head 18 which is rotatable about a primary axis 20. At least one deployable wing 22 is connected to head 18. Each deployable wing 22 is pivotable about a corresponding secondary axis 24. At least one corresponding secondary axis 24 is in a same plane as primary axis 20. Cutting head 18 has a reduced profile hemispherical shape due at least in part to material removed from cutting head 18 at cutouts 26. At least one secondary axis 24 can be approximately parallel with primary axis 20 as shown particularly in FIG. 2.

Figure 3:
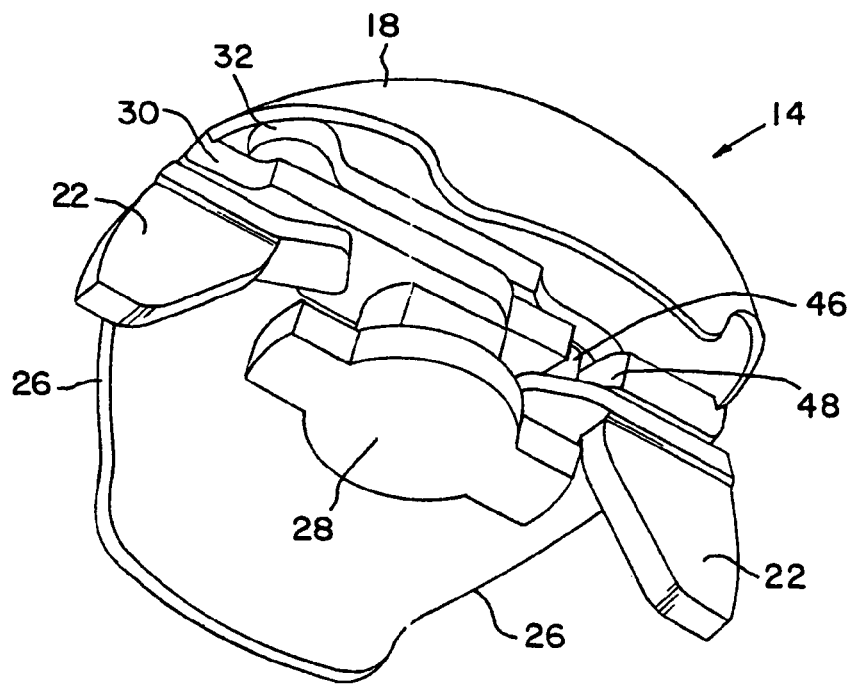
FIG. 3 is a perspective view of the orthopaedic reamer of FIGS. 1 and 2, shown with wings pivoted in an operating position.

Cutouts 26 tend to destabilize reamer 14 when reamer 14 is rotationally driven; however, orthopaedic reamer 14 is rotationally stabilized and balanced relative to primary axis 20 when deployable wings 22 are pivoted to an operating position as shown in FIGS. 1 and 3, that is when deployable wings 22 are rotated outward relative to primary axis 20. Deployable wing's 22 mass, design geometry and location relative to cutting head 18, when in an operating position as shown in FIGS. 1 and 3 where deployable wings 22 are pivoted outwardly, offset cutting head's 18 mass eliminated by cutouts 26 and thereby rotationally stabilized reamer 14 when reamer 14 is rotationally driven.

Reamer 14 additionally includes driver attachment 28, pivot arm 30, actuating cam 32, and pins 34. Driver attachment 28 includes driver attachment shaft 36 which is pivotably connected to arm shaft hole 38 and fixedly connected to cam shaft hole 40. Each pin 34 is inserted into a corresponding arm pin hole 42 and further into a corresponding wing pin hole 44 thereby allowing each deployable wing 22 to rotate about a corresponding secondary axis 24 when driver attachment 28 is pivoted about primary axis 20.

Figure 4:
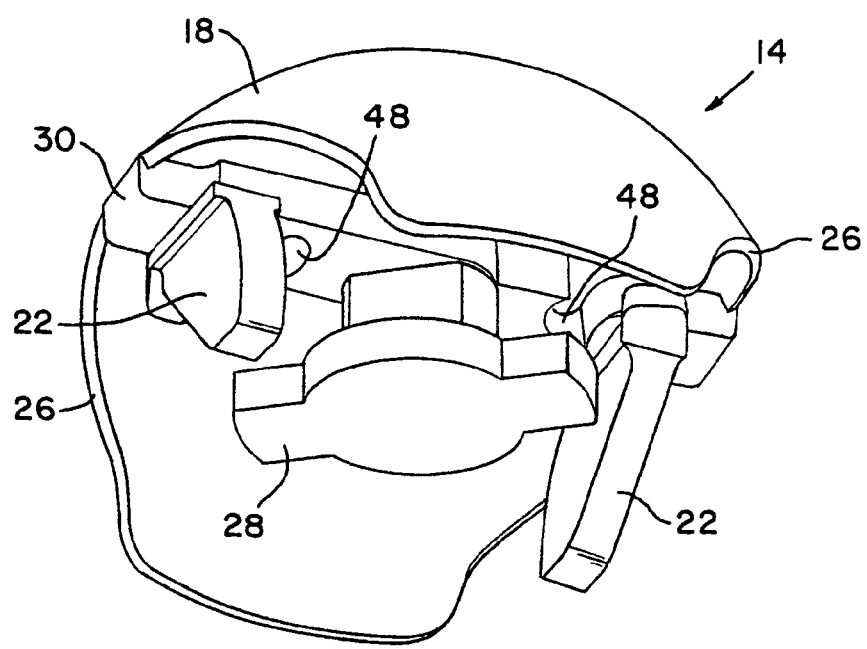
FIG. 4 is a perspective view of the orthopaedic reamer of FIG. 3, shown with wings pivoted in a nonoperating position.
Figure 5:
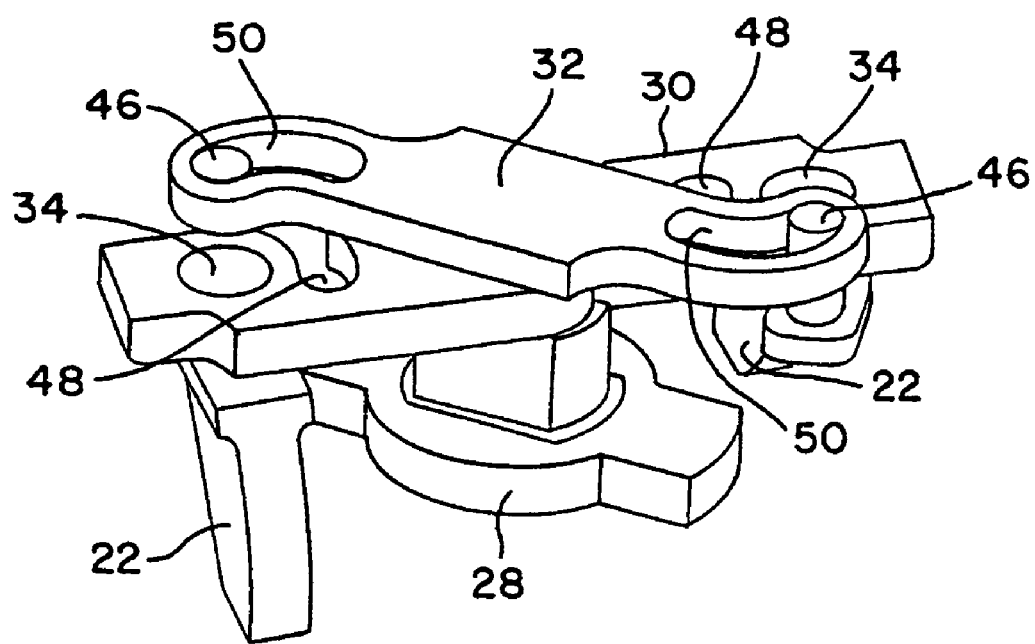
FIG. 5 is a perspective view of the deployable wings, driver attachment, pivot arm, pins and actuating cam of FIGS. 1-4.

Each wing pin 46 is inserted through a corresponding arm slot 48 and into a corresponding cam slot 50. Rotating driver attachment 28 in a cutting direction 52, which is clockwise when viewing reamer 14 as shown by arrow 54, rotates actuating cam 32 such that each wing pin 46 is motivated further into a corresponding arm slot 48, and such that each deployable wing 22 is pivoted outwardly into an operating position as shown in FIGS. 1 and 3. Rotating driver attachment 28 in a noncutting direction 56, which is counterclockwise when viewing reamer 14 as shown by arrow 54, rotates actuating cam 32 such that each wing pin 46 is motivated out of, or nearly out of, a corresponding arm slot 48, and such that each deployable wing 22 is pivoted inwardly into an nonoperating position as shown in FIGS. 4 and 5. Cutting head 18 is fixedly connected to the ends of pivot arm 30 at cutting head indents 58.

Therefore, driver attachment 28 is attachable to cutting head 18, and is configured for driving cutting head 18 in cutting direction 52, where at least one deployable wing 22 pivots about a corresponding secondary axis 24 to an operating position as shown in FIGS. 1 and 3 when cutting head 18 is driven in cutting direction 52. Additionally, driver attachment 28 is attachable to cutting head 18, and is configured for driving cutting head 18 in noncutting direction 56, where at least one deployable wing 22 pivots about a corresponding secondary axis 24 to a nonoperating position as shown in FIGS. 4 and 5 when cutting head 18 is driven in noncutting direction 56.

It is contemplated that, with suitable design changes to reamer 14, cutting direction 52 can be counterclockwise when viewed from arrow 54 and noncutting direction 56 can be clockwise when viewed from arrow 54.

Cutting head 18 can include cutting teeth (not shown), of a variety of configurations and locations, or other cutting surfaces. Further, at least one deployable wing 22 can include at least surface 60 which can be a cutting surface. Additionally, at least one deployable wing 22 can include cutting teeth (not shown), of a variety of configurations and locations, or other cutting surfaces.

In use, the present invention provides a method of using orthopaedic reamer assembly 10 including the steps of: providing reamer 14 having an at least partially hemispherical cutting head 18 which is rotatable about primary axis 20 and at least one deployable wing 22 connected to cutting head 18, where at least one deployable wing 22 is pivotable about a corresponding secondary axis 24 and at least one corresponding secondary axis 24 being in a same plane as primary axis 20; rotationally driving cutting head 18 about primary axis 20; and pivoting at least one deployable wing 22 about secondary axis 24 to an operating position. The rotationally driving step and the pivoting step can occur simultaneously. The method of the present invention can further include the step of actuating driver 12 in a noncutting direction 56 and simultaneously pivoting at least one deployable wing 22 about a corresponding secondary axis 24 to a nonoperating position. The method of the present invention can further include the step of rotationally stabilizing reamer 14 about primary axis 20. The corresponding secondary axis 24 can be in a same plane as primary axis 20, and additionally, at least one secondary axis 24 can be approximately parallel with primary axis 20.

In the embodiment shown, and when deployable wings 22 are pivoted to a nonoperating position as shown in FIGS. 4 and 5, the profile presented by orthopaedic reamer assembly 10 to a surgical incision is reduced by an amount approximately equal to the equivalent full diameter of cutting head 18 minus the length of pivot arm 30, when compared a full hemispherical reamer. Additionally, when deployable wings 22 are pivoted to an operating position as shown in FIGS. 1 and 3, reamer 14 performs a cutting operation with minimal or no degradation in cutting performance due to reamer 14 being rotationally stabilized by the deployment of deployable wings 22 to an operating position. No additional tools, force and/or action is required to deploy or retract deployable wings 22, other than operating orthopaedic reamer assembly 10 in a cutting direction 52 or noncutting direction 56, respectively.

The cutting teeth or surfaces (not shown) on cutting head 18 can extend radially from cutting head 18 a predetermined amount, for example 0.020 inches; and deployable wings 22 can extend, when in the operating position, such that the outer surfaces of deployable wings 22 can each extend radially from cutting head 18 by the same predetermined amount. Depending on the design of any cutting surfaces on either of cutting head 18 or deployable wings 22, the outer surfaces of deployable wings 22, when in the operating position, each can extend radially the same as, greater than or less than the radial extent of cutting head 18. In the embodiment shown deployable wings 22, when in the operating position, extend generally radially outward relative to primary axis 20; however, other orientations are contemplated depending on the design of deployable wings 22.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An orthopaedic reamer, comprising:
   an at least partially hemispherical cutting head which is rotatable about a primary axis;
   at least one deployable wing connected to said cutting head, each said at least one deployable wing being pivotable about a corresponding secondary axis, at least one said corresponding secondary axis being in a same plane as said primary axis; and
   a driver attachment attachable to said cutting head and configured for driving said cutting head in a cutting direction and driving said cutting head in a noncutting direction, and an interconnection between said drive attachment and said deployable wing so that said at least one deployable wing pivots about said secondary axis to an operating position when said cutting head is driven in said cutting direction and pivots about said secondary axis to a nonoperating position when said cutting head is driven in said noncutting direction.

2. The orthopaedic reamer of claim 1, wherein said cutting head has a reduced profile hemispherical shape.

3. The orthopaedic reamer of claim 1, wherein said at least one deployable wing includes at least one cutting surface.

4. The orthopaedic reamer of claim 1, wherein at least one said secondary axis is approximately parallel with said primary axis.

5. The orthopaedic reamer of claim 1, wherein said orthopaedic reamer is rotationally stabilized relative to said primary axis when said at least one deployable wing is pivoted to an operating position.

6. The orthopaedic reamer of claim 1, further including an actuating cam connected to said at least one deployable wing.

7. An orthopaedic reamer assembly, comprising:
   a driver;
   a reamer connected to said driver, said reamer including:
   an at least partially hemispherical cutting head which is rotatable about a primary axis;
   at least one deployable wing connected to said cutting head, each said at least one
   one deployable wing being pivotable about a corresponding secondary axis, at least one said corresponding secondary axis being in a same plane as said primary axis; and
   a driver attachment attachable to said cutting head and configured for driving said cutting head in a cutting direction and a noncutting direction, and an interconnection between said drive attachment and said deployable wing so that said at least one deployable wing pivots about said secondary axis to an operating position when said cutting head is driven in said cutting direction and pivots about said secondary axis to a nonoperating position when said cutting head is driven in said noncutting direction.

8. The orthopaedic reamer assembly of claim 7, wherein said cutting head has a reduced profile hemispherical shape.

9. The orthopaedic reamer assembly of claim 7, wherein said at least one deployable wing includes at least one cutting surface.

10. The orthopaedic reamer assembly of claim 7, wherein at least one said secondary axis is approximately parallel with said primary axis.

11. The orthopaedic reamer assembly of claim 7, wherein said orthopaedic reamer is rotationally stabilized relative to said primary axis when said at least one deployable wing is pivoted to an operating position.

12. The orthopedic reamer assembly of claim 7, further including an actuating cam connected to said at least one deployable wing.

13. A method of using an orthopaedic reamer assembly, comprising the steps of:
   providing a reamer including an at least partially hemispherical cutting head which is rotatable about a primary axis and at least one deployable wing connected to said cutting head, each said at least one deployable wing being pivotable about a corresponding secondary axis, at least one said corresponding secondary axis being in a same plane as said primary axis;
   rotationally driving said cutting head about said primary axis;
   pivoting said at least one deployable wing about said secondary axis to an operating position in response to rotation of said reamer in a cutting direction; and
   actuating said reamer in a noncutting direction and in response thereto simultaneously pivoting said at least one deployable wing about said secondary axis to a nonoperating position.

14. The method of claim 13, wherein said rotationally driving step and said pivoting step occur simultaneously.

15. The method of claim 13, further including the step of rotationally stabilizing said reamer about said primary axis.

16. The method of claim 13, wherein said corresponding secondary axis is in a same plane as said primary axis.

17. The method of claim 16, wherein at least one said secondary axis is approximately parallel with said primary axis.

* * * * *